(12) United States Patent
Xie et al.

(10) Patent No.: US 11,836,430 B2
(45) Date of Patent: Dec. 5, 2023

(54) FPGA-BASED RESEQUENCING ANALYSIS METHOD AND DEVICE

(71) Applicant: MGI TECH CO., LTD., Shenzhen (CN)

(72) Inventors: Yinlong Xie, Shenzhen (CN); Weihua Huang, Shenzhen (CN); Chen Chen, Shenzhen (CN); Jingbo Tang, Shenzhen (CN)

(73) Assignee: MGI TECH CO., LTD., Shenzhen (CN)

( * ) Notice: Subject to any disclaimer, the term of this patent is extended or adjusted under 35 U.S.C. 154(b) by 415 days.

(21) Appl. No.: 17/275,075

(22) PCT Filed: Oct. 23, 2018

(86) PCT No.: PCT/CN2018/111357
§ 371 (c)(1),
(2) Date: Mar. 10, 2021

(87) PCT Pub. No.: WO2020/082224
PCT Pub. Date: Apr. 30, 2020

(65) Prior Publication Data
US 2022/0058321 A1    Feb. 24, 2022

(51) Int. Cl.
*G06F 30/331*    (2020.01)
*G06F 30/20*    (2020.01)
(Continued)

(52) U.S. Cl.
CPC ........ *G06F 30/331* (2020.01); *G06F 9/30123* (2013.01); *G06F 9/345* (2013.01);
(Continued)

(58) Field of Classification Search
CPC .... G06F 30/331; G06F 9/30123; G06F 9/345; G06F 9/4881; G06F 30/20; G06N 3/126; G16B 30/10; G16B 20/20; G16B 40/00
(Continued)

(56) References Cited

U.S. PATENT DOCUMENTS

| 2013/0338934 A1 | 12/2013 | Asadi et al. |
| 2015/0012903 A1* | 1/2015 | Olgiati ................. G06F 11/263 716/136 |

(Continued)

FOREIGN PATENT DOCUMENTS

| CN | 105631239 A | 6/2016 |
| CN | 107194204 A | 9/2017 |

(Continued)

OTHER PUBLICATIONS

Search Report issued for PCT/CN2018/111357, dated Jul. 26, 2019.
(Continued)

*Primary Examiner* — Paul Dinh
(74) *Attorney, Agent, or Firm* — Westman, Champlin & Koehler, P.A.; Z. Peter Sawicki; Amanda M. Prose

(57) ABSTRACT

Proposed by the present disclosure are an FPGA-based resequencing analysis method and device, wherein the method comprises: receiving genomic resequencing data; using the resequencing data as an input of an FPGA, determining a comparison result in the resequencing process according to an output of the FPGA, and simultaneously performing sorting and deduplication processing on the comparison result; correcting a base quality value of the comparison result after sorting and deduplication processing; and detecting a mutation result according to the corrected comparison result. The described method may save program running time, save calculation costs, and improve resequencing efficiency.

8 Claims, 5 Drawing Sheets

(51) Int. Cl.
  *G06F 9/30* (2018.01)
  *G06F 9/345* (2018.01)
  *G06F 9/48* (2006.01)
  *G06N 3/126* (2023.01)
(52) U.S. Cl.
  CPC ............ *G06F 9/4881* (2013.01); *G06F 30/20* (2020.01); *G06N 3/126* (2013.01)
(58) Field of Classification Search
  USPC .................................................. 716/136, 116
  See application file for complete search history.

(56) References Cited

U.S. PATENT DOCUMENTS

2016/0259880 A1  9/2016  Semenyuk
2017/0308644 A1  10/2017  van Rooyen et al.

FOREIGN PATENT DOCUMENTS

CN   107368705 A   11/2017
CN   107609350 A   1/2018
JP   2018503164 A  2/2018

OTHER PUBLICATIONS

Written Opinion of the International Searching Authority issued for PCT/CN2018/111357, dated Jul. 26, 2019.
Search Report issued for EP patent application serial No. 18937933.2 dated Mar. 23, 2022.
Office Action issued for JP patent application serial No. 2021-519716 dated Aug. 9, 2022.

* cited by examiner

FPGA-BASED RESEQUENCING ANALYSIS METHOD AND DEVICE

CROSS-REFERENCE TO RELATED APPLICATION

The application is a national phase application of PCT Application No. PCT/CN2018/111357, filed with the State Intellectual Property Office of P. R. China on Oct. 23, 2018, the entire content of which is incorporated herein by reference.

FIELD

The present disclosure relates to the field of bioinformatics analysis technology, particularly relates to a Field-Programmable Gate Array (FPGA)-based resequencing analysis method and device.

BACKGROUND

With the emergency of the next generation gene sequencing technology, the cost of gene sequencing has dropped rapidly and the availability of sequencing data has increased. The detection and correlation study of variations in genome would promote the development in the medical field. However, the human genome is composed of more than 3 billion base pairs which are relatively large numbers. Therefore, high computing ability, storage capacity and network bandwidth are needed when sequencing and analyzing human genome.

In the related technologies, resequencing analysis includes alignment of sequencing sequences and detection of variations, where the alignment of sequencing sequences adopts a dynamic seed-and-extend algorithm. The seed length is increased to obtain fewer alignment positions when the number of that obtained by the initial seed length exceeds a fixed value. Subsequently, the Smith-Waterman algorithm is used for alignment and multiple threads are used for the detection of variations.

However, as the steps are executed serially, the execution efficiency and the analysis rate are low in the above-mentioned method.

SUMMARY

The present discourse provides in embodiments a Field Programmable Gate Array (FPGA)-based resequencing analysis method and device, to reduce program running time and calculation cost, and to improve resequencing efficiency, thereby solving the technical problems of low execution efficiency and slow analysis rate in the prior art.

In one aspect, the present disclosure provides in embodiments a FPGA-based resequencing analysis method, including:

receiving genome resequencing data;
taking the genome resequencing data as an input of an FPGA, determining an alignment result in a process of resequencing based on an output of the FPGA, and at the same time, sorting and deduplicating the alignment result;
subjecting a sorted and deduplicated alignment result to correction in accordance with a base quality value; and
detecting a variation result based on a corrected alignment result.

According to embodiments of the present disclosure, the FPGA-based resequencing analysis method receives the genome resequencing data; takes the genome resequencing data as the input of the FPGA, determines the alignment result in the process of resequencing based on the output of the FPGA, and at the same time, sorts and deduplicates the alignment result; subjects the sorted and deduplicated alignment result to correction in accordance with the base quality value; and detects the variation result based on the corrected alignment result. In embodiments of the present disclosure, the processes of aligning, sorting and deduplicating may be executed in parallel such that the program running time and calculation cost are reduced, thereby improving resequencing efficiency.

In another aspect, the present disclosure provides in embodiments a FPGA-based resequencing analysis device, including:

a receiving module, configured to receive genome resequencing data;
a processing module, configured to take the resequencing data as an input of an FPGA, to determine an alignment result in a process of resequencing based on an output of the FPGA, and at the same time, to sort and deduplicate the alignment result;
a correcting module, configured to subject a sorted and deduplicated alignment result to correction in accordance with a base quality value; and
a detecting module, configured to detect a variation result based on a corrected alignment result.

According to embodiments of the present disclosure, the FPGA-based resequencing analysis device receives genome resequencing data; takes the genome resequencing data as the input of the FPGA, determines the alignment result in the process of resequencing based on the output of the FPGA, and at the same time, sorts and deduplicates the alignment result; subjects the sorted and deduplicated alignment result to correction in accordance with the base quality value; and detects the variation result based on the corrected alignment result. In embodiments of the present disclosure, the processes of aligning, sorting and deduplicating may be executed in parallel such that the program running time and calculation cost are reduced, thereby improving resequencing efficiency.

In another aspect, the present disclosure provides in embodiments a computer device, including a memory, a processor, and a computer program stored in the memory and executable by the processor, wherein the computer program, when executed by the processor, achieves a Field-Programmable Gate Array (FPGA)-based resequencing analysis method according to above-mentioned embodiments of the present disclosure.

In another aspect, the present disclosure provides in embodiments a computer-readable storage medium having stored therein computer-readable instructions that causes the computer to perform a Field-Programmable Gate Array (FPGA)-based resequencing analysis method according to above-mentioned embodiments of the present disclosure.

The additional aspects and advantages of the present disclosure will be partially given in the following description, and some will become obvious according to the following description, or be understood through the practice of the present disclosure.

BRIEF DESCRIPTION OF THE DRAWINGS

The drawings that need to be used in examples will be briefly introduced as follows in order to describe embodiments of the present disclosure more clearly. Obviously, the drawings in the following description are some examples of the present disclosure, and other drawings can be obtained from these drawings without creative work by those skilled in the art.

DETAILED DESCRIPTION

Figure 1:
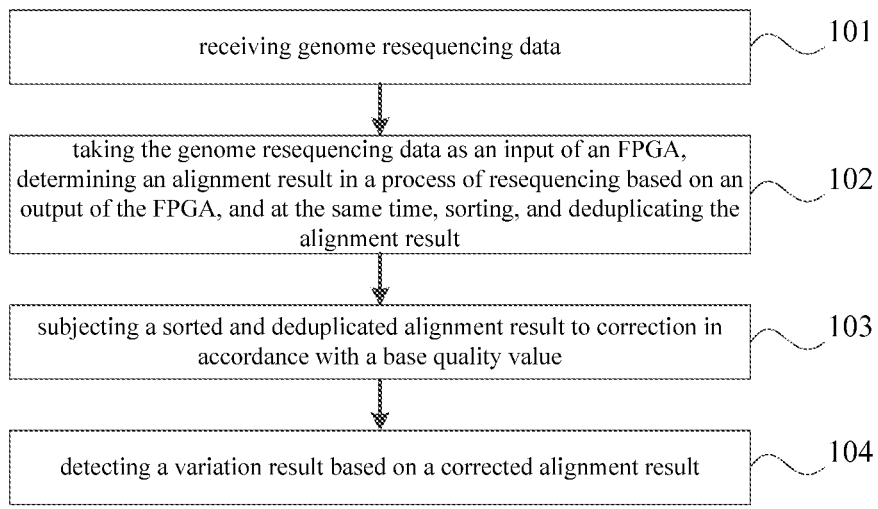
FIG. 1 is a flow chart showing a FPGA-based resequencing analysis method in the Example 1 of the present disclosure.

Reference will be made in detail to embodiments of the present disclosure. The same or similar elements and the elements having same or similar functions are denoted by like reference numerals throughout the descriptions. The embodiments described herein with reference to drawings are explanatory, illustrative, and used to generally understand the present disclosure. The embodiments shall not be construed to limit the present disclosure.

The FPGA-based resequencing analysis method and device in embodiments of the present disclosure are described below with reference to the drawings. Before describing embodiments of the present disclosure in detail, the common technical terms are defined at first in order to facilitate understanding.

Field-Programmable Gate Array (FPGA) is a configurable integrated circuit containing a programmable wiring network that connects a logic array module, an embedded memory module and a digital signal processors (abbreviated as DSP) module, while the data path and topology of a central processing unit (CPU) and a graphics processing unit (GPU) for processing program instructions are fixed. Moreover, FPGA resource may be configured and connected to establish a customized instruction pipeline to process data, such that the resulting system configuration may solve many types of computing problems efficiently. In addition, applications well-developed and used on a large scale may also rely on FPGAs as basis and verification for designing the faster but less flexible Application Specific Integrated Circuit (abbreviated as ASIC).

Resequencing refers to sequencing the respective genomes of different individuals for species with known genome sequences, based on which variations are analyzed among individuals or populations. A large number of single nucleotide polymorphism (SNP) sites, and insertion and deletion sites can be determined through the detection of variations in the sequenced genome of each individual.

FIG. 1 is a flow chart showing a FPGA-based resequencing analysis method in the Example 1 of the present disclosure.

In the present example of the present disclosure, the FPGA-based resequencing analysis method configured in the FPGA-based resequencing analysis device is taken as an example for illustration. The FPGA-based resequencing analysis device may be configured in any computer device so that the computer device may execute the FPGA-based resequencing analysis.

As shown in FIG. 1, the FPGA-based resequencing analysis method includes the following Step 101 to Step 104.

At Step 101: genome resequencing data is received.

In examples of the present disclosure, the genome resequencing data includes basic genome resequencing data and parameter information describing the basic genome resequencing data.

Optionally, the genome resequencing data may be written into a preset file in advance which may be read when a genome is resequenced, thereby obtaining the genome resequencing data based on the preset file.

Further, the preset file is saved as a compressed file generally, for example, in a format such as gz. Therefore, the preset file may also be decompressed before being read.

At Step 102: the genome resequencing data is taken as an input of an FPGA, an alignment result in a process of resequencing is determined based on an output of the FPGA, and at the same time, the alignment result is sorted and deduplicated.

In examples of the present disclosure, the genome resequencing data may be aligned to a reference genome to obtain information such as alignment positions. The obtained information then may be transmitted to the FPGA for calculation to obtain the alignment result. As a possible implementation, in order to improve the alignment efficiency, it may rely on the parallel processing property of the FPGA, dividing the genome resequencing data into multiple subsets of genome resequencing sub- with a fixed length, aligning the multiple subsets of genome resequencing data with the fixed length to the reference genome in parallel to obtain multiple subsets of alignment results; and combining the multiple sub-sets of alignment sub-results to obtain the alignment result.

The alignment result, when obtained, may be at the same time sorted according to the alignment positions on the reference genome, and those genome resequencing data aligned to a same position may be deduplicated. The reason is that duplicate genome resequencing data affects comparison and evaluation of alignment such as a sequencing depth, and eventually leads to a false positive in the detection of variations. Therefore, the genome resequencing data aligned to a same position may be deduplicated.

Optionally, the genome resequencing data may be aligned by calling a bioinformatics software and an alignment script, to determine the alignment result in the process of resequencing. The alignment result is then sorted and deduplicated by a bioinformatics software and a sorting and deduplicating script, to determine a sorted and deduplicated alignment result. The bioinformatics software includes BuildAlignerIndex, Alignment, SortMarkDup, BuildBQSRIndex, BQSR, and HaplotypeCaller, etc.

For example, the genome resequencing data may be aligned by a FPGA-accelerated high-performance DNA sequence alignment software that supports alignment of paired-end short reads in a length of 33 to 160 bp. The alignment result may be sorted and deduplicated by a multi-thread-accelerated high-performance sorting and deduplicating software that supports input and output of a pipe, thereby improving efficiency of sorting and deduplicating.

In examples of the present disclosure, the processes of aligning, sorting and deduplicating may be executed in parallel, thus reducing program running time and calculation cost, thereby improving resequencing efficiency.

At Step 103: a sorted and deduplicated alignment result is subjected to correction in accordance with a base quality value.

In examples of the present disclosure, in order to make the alignment result close to reality in accordance with the base quality value and reduce a probability of mismatches to the reference genome, the sorted and deduplicated alignment result may be corrected in accordance with the base quality value, i.e., the sorted and deduplicated alignment result is corrected in accordance with the base quality value within the genome resequencing data.

Optionally, the sorted and deduplicated alignment result may be corrected in accordance with the base quality value by calling a bioinformatics software and a base quality value correcting script, to obtain a corrected alignment result. For example, the sorted and deduplicated alignment result may be corrected in accordance with the base quality value by a multi-thread-accelerated high-performance base quality value correcting software that supports input and output of a pipe, thereby improving correction efficiency.

At Step 104: a variation result is detected based on a corrected alignment result.

In examples of the present disclosure, detection of the variation result includes detection of a single nucleotide polymorphism (SNP) site and detection of insertion and deletion sites. The variation result may be detected based on the corrected alignment result and related information.

Optionally, the variation result may be detected based on the corrected alignment result by calling a bioinformatics software and a variation detecting script, to determine a detection result. For example, the variation result may be detected based on the corrected alignment result by a FPGA-accelerated high-performance variation detecting software, to obtain a variation detecting result, thereby improving efficiency of variation detection.

According to the example of the present disclosure, the FPGA-based resequencing analysis method receives the genome resequencing data; takes the genome resequencing data as the input of the FPGA, determines the alignment result in the process of resequencing based on the output of the FPGA, and at the same time, sorts and deduplicates the alignment result; subjects the sorted and deduplicated alignment result to correction in accordance with the base quality value; and detects the variation result based on the corrected alignment result. In embodiments of the present disclosure, the processes of aligning, sorting and deduplicating may be executed in parallel such that the program running time and calculation cost are reduced, thereby improving resequencing efficiency.

As a possible implementation, after the genome resequencing data is received, the genome resequencing data may be further subjected to hash-calculation based on a sequence of a preset length, and hash-calculated genome resequencing data is taken as the input of the FPGA. Therefore, it is possible to fast locate the alignment position in the reference genome, thereby reducing random access to memory and thus improving alignment efficiency In order to illustrate the above example more clearly, the present disclosure provides in an example another FPGA-based resequencing analysis method.

Figure 2:
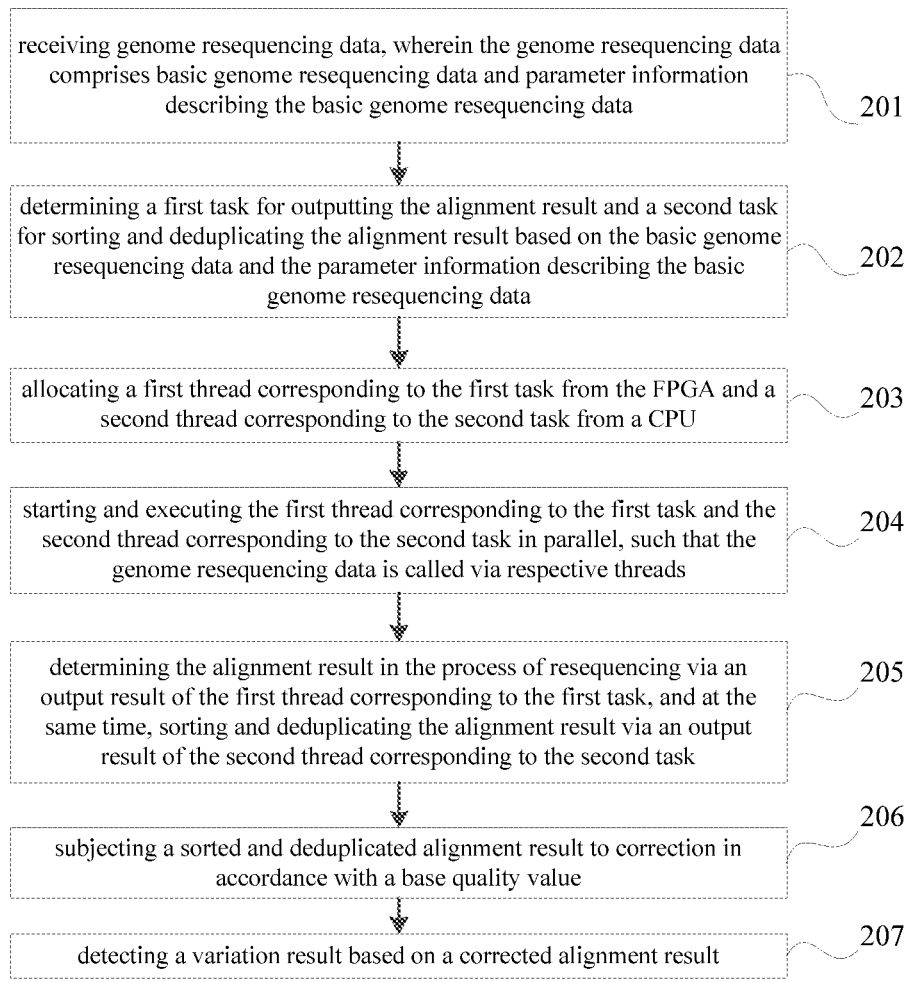
FIG. 2 is a flow chart showing a FPGA-based resequencing analysis method in the Example 2 of the present disclosure.

FIG. 2 a flow chart showing a FPGA-based resequencing analysis method in the Example 2 of the present disclosure.

As shown in FIG. 2, the FPGA-based resequencing analysis method may include the following Step 201 to Step 207.

At Step 201: genome resequencing data is received, where the genome resequencing data includes basic genome resequencing data and parameter information describing the basic genome resequencing data.

Figure 3:
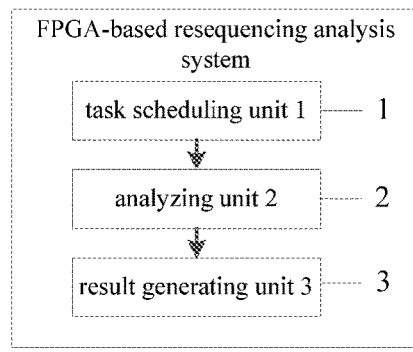
FIG. 3 is a schematic diagram 1 showing a FPGA-based resequencing analysis system according to examples of the present disclosure.

For example, FIG. 3, to which is referred, is a schematic diagram 1 showing a FPGA-based resequencing analysis system according to examples of the present disclosure, where the resequencing analysis system includes a task scheduling unit 1, an analyzing unit 2 and a result generating unit 3. The task scheduling unit 1 is configured to receive the basic genome resequencing data and the parameter information describing the basic genome resequencing data.

At Step 202: a first task for outputting the alignment result and a second task for sorting and deduplicating the alignment result are determined based on the basic genome resequencing data and the parameter information describing the basic genome resequencing data.

In examples of the present disclosure, the processes of aligning, sorting and deduplicating are executed in parallel, thus reducing program running time and calculation cost, thereby improving resequencing efficiency. Therefore, once the genome resequencing data is received, the first task for outputting the alignment result and the second task for sorting and deduplicating the alignment result both may be determined in parallel based on the basic genome resequencing data and the parameter information describing the basic genome resequencing data.

For example, referring to FIG. 3, the task scheduling unit 1 may be configured to determine both the first task for outputting the alignment result and the second task for sorting and deduplicating the alignment result in parallel based on the basic genome resequencing data and the parameter information describing the basic genome resequencing data. The first task and the second task may be then sent to the analyzing unit 2, which is process-scheduled. For example, the analyzing unit 2 may be process-scheduled by a bioinformatics software and a system scheduling script.

At Step 203: a first thread corresponding to the first task and a second thread corresponding to the second task are allocated from the FPGA and a CPU, respectively.

In examples of the present disclosure, after the first task and the second task are determined, the first thread corresponding to the first task and the second thread corresponding to the second task may be allocated from the FPGA and the CPU, respectively.

At Step 204: the first thread corresponding to the first task and the second thread corresponding to the second task are started and executed in parallel, such that the genome resequencing data is called via respective threads.

In examples of the present disclosure, the first thread corresponding to the first task and the second thread corresponding to the second task, after determined, may be started and executed in parallel, such that the genome resequencing data is called via respective threads for aligning, sorting and deduplicating.

At Step 205: the alignment result in the process of resequencing is determined via an output result of the first thread corresponding to the first task, and at the same time, the alignment result is sorted and deduplicated via an output result of the second thread corresponding to the second task.

In examples of the present disclosure, after the genome resequencing data is called via the first thread corresponding to the first task, the alignment result in the process of resequencing may be determined based on the output result of the first thread corresponding to the first task. As a possible implementation, the first thread corresponding to the first task may be executed to determine a targeted alignment position, the alignment on duplicate base pairs in the basic genome resequencing data is triggered in accordance with the targeted alignment position, and an alignment result of the duplicate base pairs is taken as the alignment result in the process of resequencing. For example, referring to FIG. 3, the analyzing unit 2 may be configured to analyze the genome resequencing data to determine the alignment result by process-calling a bioinformatics software and an alignment script, by accelerating the software and by calling the first thread corresponding to the first task from the FPGA.

In examples of the present disclosure, the alignment result may be called via the second thread corresponding to the second task for sorting and deduplicating. For example, referring to FIG. 3, the analyzing unit 2 may be configured to sort and deduplicate the alignment result by process-calling a bioinformatics software and a sorting and deduplicating script, by accelerating the software and by calling the second thread corresponding to the second task from the CPU.

At Step 206: a sorted and deduplicated alignment result is subjected to correction in accordance with a base quality value.

At Step 207: a variation result is detected based on a corrected alignment result.

For example, referring to FIG. 3, the analyzing unit 2 may be configured to correct the sorted and deduplicated alignment result in accordance with the base quality value by process-calling a bioinformatics software and a base quality value correcting script. Further, the analyzing unit 2 may be configured to detect the variation result based on the corrected alignment result to determine a variation detecting result by process-calling a bioinformatics software and a variation detecting script.

Further, referring to FIG. 3, after the variation detecting result is obtained, the result generating unit 3 is configured to send the variation detecting result from the analyzing unit 2 to a designated location based on the parameter information describing the basic genome resequencing data transmitted by the task scheduling unit 1.

In examples of the present disclosure, the genome resequencing data is analyzed by calling a bioinformatics software and a personalized analyzing script, by accelerating the software and by calling resources from the FPGA, thereby improving efficiency of genome resequencing.

Figure 4:
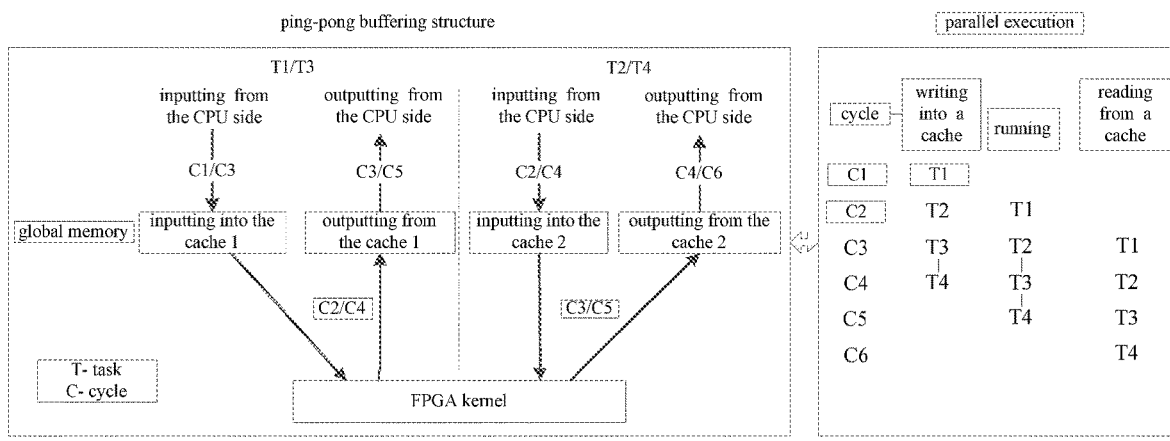
FIG. 4 is a schematic diagram showing acceleration using a ping-pong buffering technology according to examples of the present disclosure.

As a possible implementation, the targeted alignment position may be cached by a ping-pong buffering technology. For example, FIG. 4, to which is referred, is a schematic diagram showing acceleration using a ping-pong buffering technology according to examples of the present disclosure. The data in a global memory of the FPGA is cached using the ping pong buffer technology. The reason is that a reading/writing operation in the global memory of the FPGA by the CPU may be performed in parallel with a calculating operation by a FPGA kernel module, thereby improving running efficiency.

If the traditional serial execution mode of "writing a global memory→running a kernel→reading the global memory" is used, a calculating module of the FPGA would be in a state of waiting for Input/Output (I/O) for a period of time, leading to low running efficiency. Therefore, using the ping pong buffer technology to cache the data in the FPGA global memory, such as the targeted alignment position, may keep the calculating module of the FPGA always in an efficient working state, and allow multiple subtasks of a single task to be executed in pipeline, thus achieving parallel execution of the task. For example, referring to FIG. 4, the task T1 being read and output from the cache 1, the task T2 being data-calculated by the cache 2, and the task T3 being written and input into the cache 1 are performed in parallel at the time slice C3.

Figure 5:
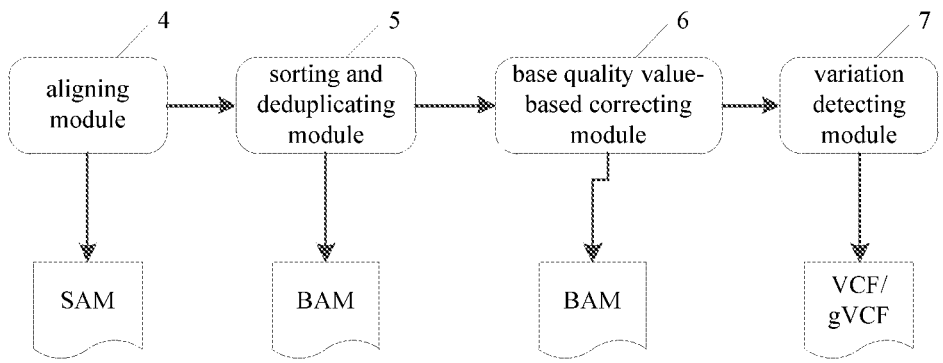
FIG. 5 is a schematic diagram 2 showing a FPGA-based resequencing analysis system according to examples of the present disclosure.

As an example, FIG. 5, to which is referred, is a schematic diagram 2 showing a FPGA-based resequencing analysis system according to examples of the present disclosure. The FPGA-based resequencing analysis system includes an aligning module 4, a sorting and deduplicating module 5, a base quality value-based correcting module 6 and a variation detecting module 7.

The aligning module 4 is configured to align received genome resequencing data to the reference genome; and to transmit aligned data to the FPGA for calculation, thereby obtaining the alignment result, which may be stored in a SAM format file.

The sorting and deduplicating module 5 is configured to sort the data output from the aligning module 4 in accordance with the alignment positions; and to mark and filter the duplicate data. The sorted and deduplicated alignment results may be stored in a BAM format file.

The base quality value-based correcting module 6 is configured to correct the data output from the sorting and deduplicating module 5 in accordance with the base quality value. The corrected alignment result may be stored in a BAM format file.

The variation detecting module 7 is configured to detect a variation result based on the data output from the base quality value-based correcting module 6 by calling a bioinformatics software and an analyzing script. The detection of the variation result includes detection of a single nucleotide polymorphism (SNP) site and detection of insertion and deletion sites. The variation detecting result may be stored in a VCF or gVCF format file.

Figure 6:
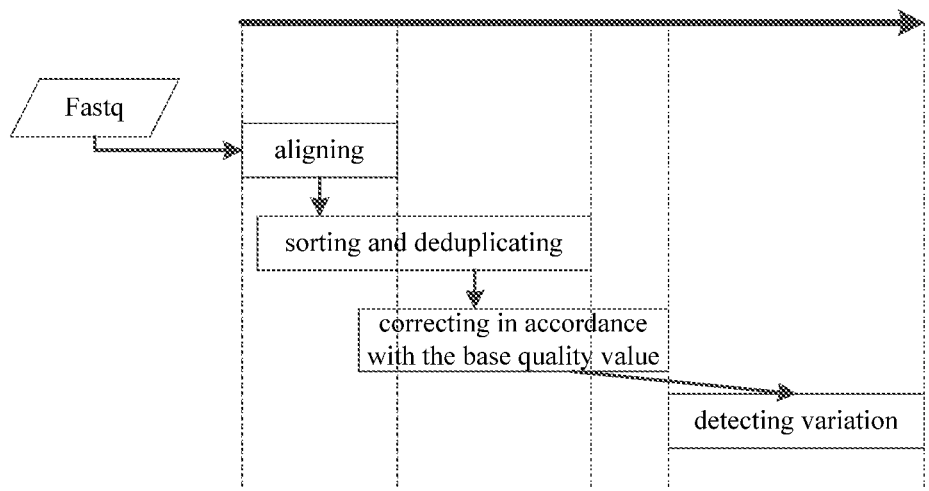
FIG. 6 is a schematic diagram of running timing sequence according to examples of the present disclosure.

FIG. 6, to which an example is referred, is a schematic diagram of running timing sequence according to examples of the present disclosure. In FIG. 6, with a Fastq input file, the entire calculation process is optimized as a pipeline structure by adjusting the calculation modes of data between adjacent steps and adding corresponding input and output buffers.

Specifically, the aligning module, running at the start of the program, is configured to align the genome resequencing data in the input file to the reference genome to obtain the alignment result, which is output to the sorting and deduplicating module.

The sorting and deduplicating module, running at the same time with the aligning module, is configured to sort the data output from the aligning module in accordance with the alignment positions; and to mark and filter the duplicate data.

The base quality value-based correcting module, running at the same time with the sorting and deduplicating module after alignment is completed in the alignment module, is configured to correct the data output from the sorting and deduplicating module in accordance with the base quality value.

The variation detecting module is configured to detect a variation result based on the data output from the base quality value-based correcting module by calling a bioinformatics software and an analyzing script. The detection of the variation result includes detection of a single nucleotide polymorphism (SNP) site and detection of insertion and deletion sites.

In examples of the present disclosure, the genome resequencing analysis is accelerated by process-calling the bioinformatics software and the analyzing script, thus improving efficiency of genome resequencing.

Figure 7:
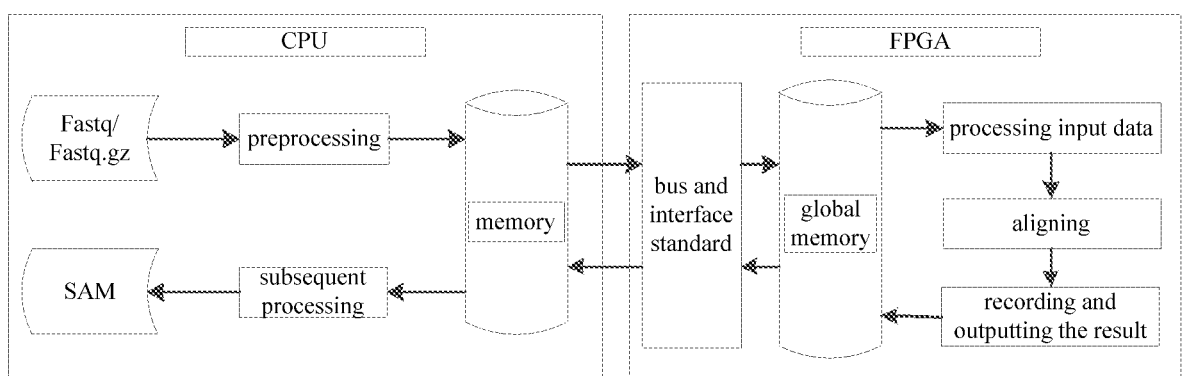
FIG. 7 is a schematic diagram 3 showing a FPGA-based resequencing analysis system according to examples of the present disclosure.

FIG. 7, to which an example is referred, is a schematic diagram 3 showing a FPGA-based resequencing analysis system according to examples of the present disclosure.

The CPU side reads the input file (Fastq), stores the data that needs to be calculated in the memory, and transmits the data in the memory to the global memory of the FPGA through the bus and interface standard. In the FPGA, the input data is processed and aligned, and the result is recorded, output, and stored in the global memory. The FPGA then transmits the processed data to the memory at the CPU side through the bus and interface standard for subsequent processing, and outputs the SAM format file.

In examples of the present disclosure, the genome resequencing data is aligned at a high speed by independent configuration of CPU and FPGA, where CPU achieves preprocessing and subsequent processing of data in parallel through the multi-thread technology, and FPAG achieves fine-grained pipeline processing by multiple functional modules connected with channels.

As a possible implementation, the I/O reading and writing operations may be separated from compression/decompression operations. The compression/decompression operations may be calculated in parallel with loop caching and multi-threading, thereby improving efficiency of genome resequencing.

Figure 8:
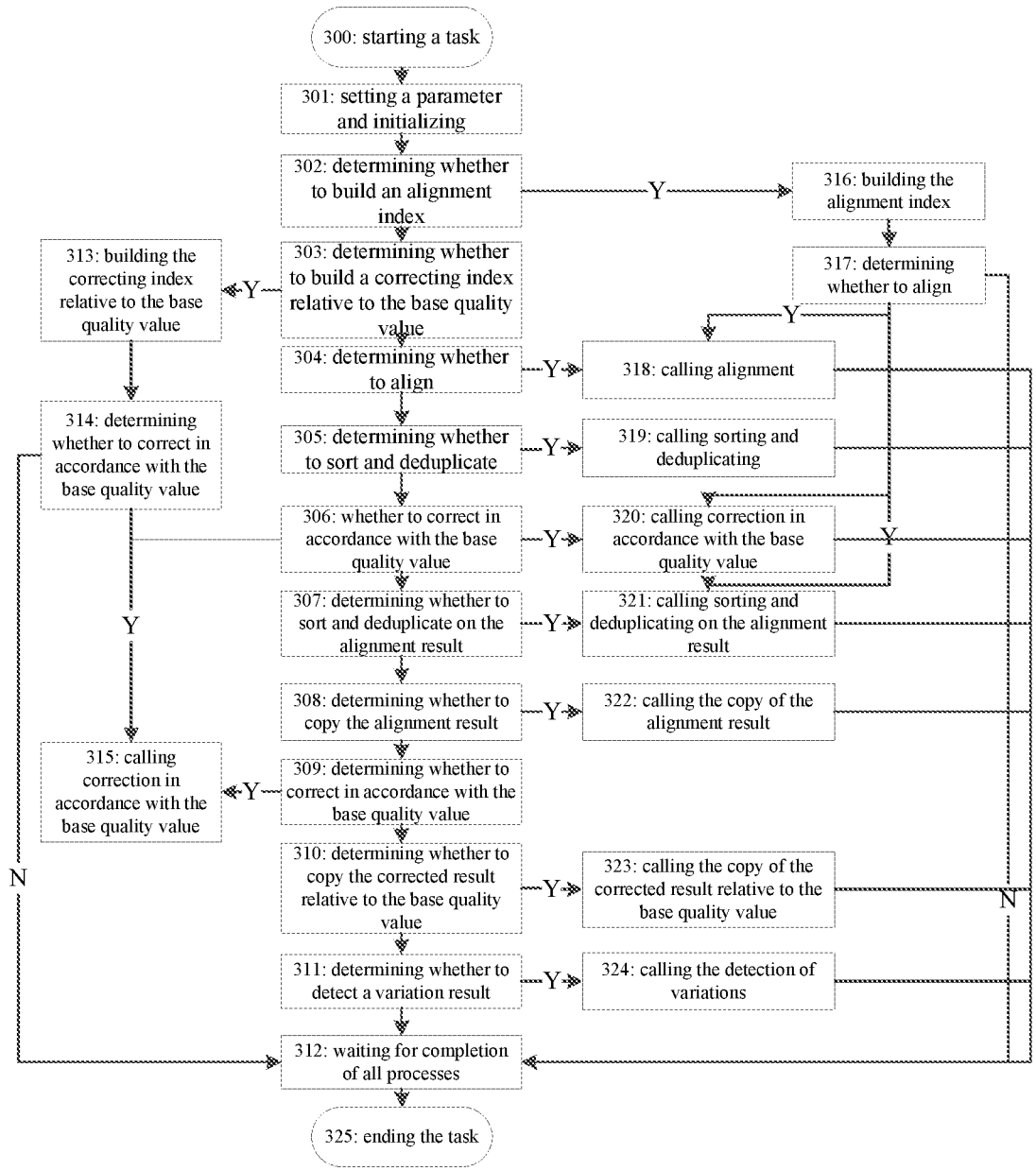
FIG. 8 is a flow chart showing a FPGA-based resequencing analysis method in the Example 3 of the present disclosure.

FIG. 8, to which an example is referred, is a flow chart showing a FPGA-based resequencing analysis method in the Example 3 of the present disclosure.

As shown in FIG. 8, the FPGA-based resequencing analysis method may include the following steps:

300: starting a task;

301: calling a program, setting a parameter and initializing, wherein in specific it may start scheduling a task to receive the basic genome resequencing data and the parameter information describing the basic genome resequencing data after all parameter are initialized;

302: determining whether to build an alignment index, if yes, executing the step 316;

303: determining whether to build a correcting index relative to the base quality value, if yes, executing the step 313;

304 or 317: determining whether to align, if yes, executing the step 318;

305: determining whether to sort and deduplicate, if yes, executing the step 319;

306: determining whether to correct in accordance with the base quality value, if yes, executing the step 320;

307: determining whether to sort and deduplicate on the alignment result, if yes, executing the step 321;

308: determining whether to copy the alignment result, if yes, executing the step 322;

309 or 314: determining whether to correct in accordance with the base quality value, if yes, executing the step 315;

310: determining whether to copy the corrected result relative to the base quality value, if yes, executing the step 323;

311: determining whether to detect a variation result, if yes, executing the step 324;

312: waiting for completion of all processes;

313: building the correcting index relative to the base quality value;

315: calling correction in accordance with the base quality value;

316: building the alignment index, used for aligning the genome resequencing data to the reference genome rapidly;

318: calling alignment, where the CPU side aligns the genome resequencing data to the reference genome to obtain information such as the alignment positions and transmits the obtained data to FPGA for alignment, and the FPGA sends the alignment result to the CPU side;

319: calling sorting and deduplicating;

320: calling correction in accordance with the base quality value, to make the alignment result close to reality in accordance with the base quality value and reduce the probability of mismatches to the reference genome;

321: calling sorting and deduplicating on the alignment result, where duplicate reads in the alignment result, produced mainly by PCR in sequencing, are filtered in accordance with the alignment positions (as the duplicate reads affects comparison and evaluation of alignment such as a sequencing depth, and eventually leads to a false positive in the detection of variations), and the sorted and deduplicated alignment result is normally stored in a BAM format file.

322: calling the copy of the alignment result, which may be called backstage;

323: calling the copy of the corrected result relative to the base quality value, which may be called backstage;

324: calling the detection of variations;

325: ending the task.

It should be noted that in a hardware, a FPGA accelerator card or a GPU may also be used to improve resequencing efficiency. Moreover, the FPGA-based resequencing analysis system of the present disclosure is composed of multiple modules, improvement, modification, or replacement to any module method, such as using the bwt algorithm to replace the above-described alignment, is within the protection scope of the present disclosure. Therefore, both the hardware-accelerated bwt algorithm and the bwt algorithm replacing the above-described alignment directly can achieve the technical effects of the present disclosure.

As an example, the following public data is used for testing.

The web path of the data is http://gigadb.org/dataset/100274

The data path is ftp://parrot.genomics.cn/gigadb/pub/10.5524/100001_101000/100274/CL100008589_L02_read_1.fq.gz ftp://parrot.genomics.cn/gigadb/pub/10.5524/100001_101000/100274/CL100008589_L02_read_2.fq.gz.

The process of BWA+GATK in the related technology is as follows:

1. aligning, sorting and deduplicating the command lines for aligning and sorting are as follows:
./BIN/bwa-0.7.13/bwa mem -t 72 -M -Y \
  -R "@RG\tID:PE100\tPL:Illumina\tPU:PE100\tLB:NA12878\tSM:PE100\tCN:NIST" \
  ./REF_hs37d5/hs37d5/hs37d5.fa \
  ./read_1.fq.gz ./read_2.fq.gz \
| ./BIN/samtools-1.3/bin/samtools view -buhS \
  -t ./REF_hs37d5/hs37d5/hs37d5.fa.fai - \

| ./BIN/samtools-1.3/bin/samtools sort -m 1000000000 \
   \
-T ./PE100.sort \
-o ./PE100.1.sorted.bam -;
the command lines for deduplicating are as follows:
./BIN/jdk1.8.0_131/bin/java -jar ./BIN/picard.jar Mark-
   Duplicates \
   I=./PE100.1.sorted.bam \
   O=./PE100.2.rmdup.bam \
   M=./PE100.2.rmdup.mat \
   REMOVE_DUPLICATES=false \
TMP_DIR=./tmp;
the command lines for building an index are as follows:
./BIN/samtools-1.3/bin/samtools index \
./PE100.2.rmdup.bam;
2. correction in accordance with the base quality value
./BIN/jdk1.8.0_131/bin/java
   -jar ./GATK_stat/lib/GenomeAnalysisTK.3.7-0/Ge-
      nomeAnalysisTK.jar \
      --disable_auto_index_creation_and_locking_
         when_reading_rods \
   -T BaseRecalibrator \
   -nct 72 \
   -R REF_hs37d5/hs37d5/hs37d5.fa \
   -I ./PE100.2.rmdup.bam \
   -o ./PE100.4.bqsr.grp \
-knownSites ./REF_hs37d5/GATK.b37/
   Mills_and_1000G_gold_standard.indels.b37.vcf \
-knownSites./REF_hs37d5/GATK.b37/
   1000G_phase1.indels.b37.vcf \
-knownSites./REF_hs37d5/dbsnp_GRCh37_b149/
   dbsnp-149.vcf
PrintReads:
./BIN/jdk1.8.0_131/bin/java
-jar IGATK_stat/lib/GenomeAnalysisTK.3.7-0/Genom-
   eAnalysisTK.jar \
   --disable_auto_index_creation_and_locking_
      when_reading_rods \
   -T PrintReads \
   -nct 72 \
   -R REF_hs37d5/hs37d5/hs37d5.fa \
   -I ./PE100.2.rmdup.bam \
   -BQSR ./PE100.4.bqsr.grp \
   -o./PE100.4.bqsr.bam \
   -baqGOP 30
the command lines for building an index is as follows:
./BIN/samtools-1.3/bin/samtools index \
   ./PE100.4.bqsr.bam; and
3. detection of variations
./BIN/jdk1.8.0_131/bin/java
-jar./GATK_stat/lib/GenomeAnalysisTK.3.7-0/Genom-
   eAnalysisTK.jar \
   --disable_auto_index_creation_and_locking_
      when_reading_rods \
-R REF_hs37d5/hs37d5/hs37d5.fa \
-T HaplotypeCaller \
-nct 72 \
-I ./PE100.4.bqsr.bam \
--dbsnp IREF_hs37d5/dbsnp_GRCh37_b149/dbsnp-
   149.vcf \
-stand_call_conf 10.0 \
-o ./raw.snp_jndel.vcf.
The process of the present disclosure is as follows:
MegaBOLT -type allwithindex -list ./my.list -scalafile
   ./my.scala
   -ref ./REF_hs37d5/hs37d5/hs37d5.fa -alignerindex
      ./REF_hs37d5/hs37d5/hs37d5.fa
   -bqsrindex ./REF_hs37d5/hs37d5/bqsrRef
   -vcf ./REF_hs37d5/dbsnp_GRCh37_b149/dbsnp-
      149.vcf.

TABLE 1

Comparison of process running time

| Dataset | Number of base pairs (Gbp) | Process | Running time (hour) |
|---|---|---|---|
| Paired-end 100 bp | 114 | MegaBOLT | 2.4 |
| | | BWA + GATK | 59.0 |

TABLE 2

Evaluation and comparison of the variation detecting result

| | | SNPs | | | | | INDELs | | | | |
|---|---|---|---|---|---|---|---|---|---|---|---|
| Dataset | Process | True positive | False positive | False negative | Accuracy | Sensitivity | True positive | False positive | False negative | Accuracy | Sensitivity |
| Paired-end 100 bp | MegaBOLT | 3,201,059 | 15,401 | 9,198 | 99.52% | 99.71% | 461,465 | 27,966 | 19,801 | 94.29% | 95.89% |
| | BWA + GATK | 3,201,095 | 6,987 | 9,162 | 99.78% | 99.71% | 462,450 | 17,681 | 18,817 | 96.32% | 96.09% |

It can be seen from the above results that, as shown in Table 1, the running time consumed by the claimed method of the present disclosure is about 20 times faster than that in the related technology; as shown in Table 2, the accuracy and sensitivity in SNP detection by the claimed method of the present disclosure are basically as same as that in the related technology; meanwhile although the accuracy in INDEL detection by the claimed method of the present disclosure is slightly worse than that in the related technology, the sensitivity basically maintains. Therefore, the overall result obtained by the claimed method of the present discourse is equivalent to the related technology.

In order to implement the above examples, the present disclosure further provides in an example a FPGA-based resequencing analysis device.

Figure 9:
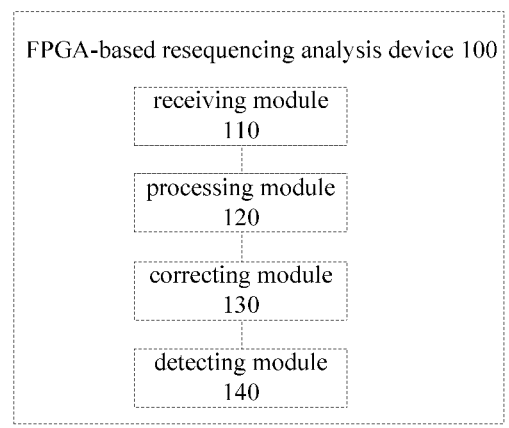
FIG. 9 is a schematic diagram showing a FPGA-based resequencing analysis device in the Example 4 of the present disclosure.

FIG. 9 is a schematic diagram showing a FPGA-based resequencing analysis device in the Example 4 of the present disclosure.

As shown in FIG. 9, the FPGA-based resequencing analysis device 100 includes a receiving module 101, a processing module 120, a correcting module 130 and a detecting module 140.

The receiving module 101 is configured to receive genome resequencing data.

The processing module 120 is configured to take the resequencing data as an input of an FPGA, to determine an alignment result in a process of resequencing based on an output of the FPGA, and at the same time, to sort and deduplicate the alignment result.

The correcting module 130 is configured to subject a sorted and deduplicated alignment result to correction in accordance with a base quality value.

The detecting module 140 is configured to detect a variation result based on a corrected alignment result.

Figure 10:
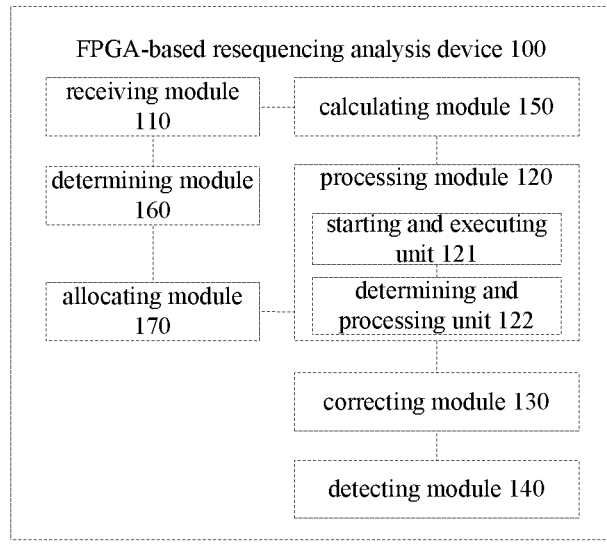
FIG. 10 is a schematic diagram showing a FPGA-based resequencing analysis device in the Example 5 of the present disclosure.

Further, as a possible implementation of the present discourse, referring to FIG. 10 on the basis of FIG. 9, the FPGA-based resequencing analysis device 100 may further include: a calculating module 150, configured to subject the genome resequencing data to hash-calculation based on a sequence of a preset length after the genome resequencing data is received.

Accordingly, the processing module 120 is specifically configured to take hash-calculated genome resequencing data as the input of the FPGA.

As a possible implementation, the genome resequencing data include basic genome resequencing data and parameter information describing the basic genome resequencing data.

The FPGA-based resequencing analysis device 100 may further include:
- a determining module 160, configured to determine a first task for outputting the alignment result and a second task for sorting and deduplicating the alignment result based on the basic genome resequencing data and the parameter information describing the basic genome resequencing data after the genome resequencing data is received; and
- an allocating module 170, configured to allocate a first thread corresponding to the first task from the FPGA and a second thread corresponding to the second task from a CPU.

As a possible implementation, the processing module 120 includes:
- a starting and executing unit 121, configured to start and execute the first thread corresponding to the first task and the second thread corresponding to the second task in parallel, so as to call the genome resequencing data via respective threads; and
- a determining and processing unit 122, configured to determine the alignment result in the process of resequencing via an output result of the first thread corresponding to the first task, and at the same time, to sort and deduplicate the alignment result via an output result of the second thread corresponding to the second task.

As a possible implementation, the determining and processing unit 122 is specifically configured to execute the first thread corresponding to the first task to determine a targeted alignment position; to trigger alignment on duplicated base pairs in the basic genome resequencing data in accordance with the targeted alignment position; and to take an alignment result of the duplicated base pairs as the alignment result in the process of resequencing.

As a possible implementation, the determining and processing unit 122 is further configured to cache the targeted alignment position by using a ping-pong buffering technology.

It should be noted that the above explanation and illustration for the FPGA-based resequencing analysis method in embodiments are also applicable to the FPGA-based resequencing analysis device 100 of the subsequent embodiments, which will not be repeated here.

According to embodiments of the present disclosure, the FPGA-based resequencing analysis device receives genome resequencing data; takes the genome resequencing data as the input of the FPGA, determines the alignment result in the process of resequencing based on the output of the FPGA, and at the same time, sorts and deduplicates the alignment result; subjects the sorted and deduplicated alignment result to correction in accordance with the base quality value; and detects the variation result based on the corrected alignment result. In embodiments of the present disclosure, the processes of aligning, sorting and deduplicating may be executed in parallel such that the program running time and calculation cost are reduced, thereby improving resequencing efficiency.

In order to implement the above examples, the present disclosure further provides in an example a computer device, including: a memory; a processor, and a computer program stored in the memory and executable by the processor, wherein the computer program, when executed by the processor, achieves a Field-Programmable Gate Array (FPGA)-based resequencing analysis method in the above-mentioned embodiments of the present disclosure.

In order to implement the above examples, the present disclosure further provides in an example a computer-readable storage medium having stored therein computer-readable instructions that causes the computer to perform a Field-Programmable Gate Array (FPGA)-based resequencing analysis method in the above-mentioned embodiments of the present disclosure.

Reference throughout this specification to "an embodiment", "some embodiments", "one embodiment", "another example", "an example", "a specific example" or "some examples" means that a particular feature, structure, material, or characteristic described in connection with the embodiment or example is included in at least one embodiment or example of the present disclosure. Thus, the appearances of the phrases such as "in some embodiments", "in one embodiment", "in an embodiment", "in another example", "in an example", "in a specific example" or "in some examples", in various places throughout this specification are not necessarily referring to the same embodiment or example of the present disclosure. Furthermore, the particular features, structures, materials, or characteristics may be combined in any suitable manner in one or more embodiments or examples. In addition, those skilled in the art can combine different embodiments or examples and features in different embodiments or examples without contradicting each other.

In addition, terms such as "first" and "second" are used herein for purposes of description and are not intended to indicate or imply relative importance or significance or impliedly indicate quantity of the technical feature referred to. Thus, the feature defined with "first" and "second" may comprise one or more this features. In the description of the present disclosure, "a plurality of" means two or more than two this features, unless specified otherwise.

Any procedure or method described in the flow charts or described in any other way herein may be understood to comprise one or more modules, portions or parts for storing executable codes that realize particular logic functions or procedures. Moreover, advantageous embodiments of the present disclosure comprises other implementations in which the order of execution is different from that which is depicted or discussed, including executing functions in a substantially simultaneous manner or in an opposite order according to the related functions. This should be understood by those skilled in the art to which embodiments of the present disclosure belong.

The logic and/or step described in other manners herein or shown in the flow chart, for example, a particular sequence table of executable instructions for realizing the logical function, may be specifically achieved in any computer readable medium to be used by the instruction execution system, device or equipment (such as the system based on computers, the system comprising processors or other systems capable of obtaining the instruction from the instruction execution system, device and equipment and executing the instruction), or to be used in combination with the instruction execution system, device and equipment. As to the specification, "the computer readable medium" may be any device adaptive for including, storing, communicating, propagating or transferring programs to be used by or in combination with the instruction execution system, device or equipment. More specific examples of the computer readable medium comprise but are not limited to: an electronic connection (an electronic device) with one or more wires, a portable computer enclosure (a magnetic device), a random access memory (RAM), a read only memory (ROM), an erasable programmable read-only memory (EPROM or a flash memory), an optical fiber device and a portable compact disk read-only memory (CDROM). In addition, the computer readable medium may even be a paper or other appropriate medium capable of printing programs thereon, this is because, for example, the paper or other appropriate medium may be optically scanned and then edited, decrypted or processed with other appropriate methods when necessary to obtain the programs in an electric manner, and then the programs may be stored in the computer memories.

It should be understood that each part of the present disclosure may be realized by the hardware, software, firmware or their combination. In the above embodiments, a plurality of steps or methods may be realized by the software or firmware stored in the memory and executed by the appropriate instruction execution system. For example, if it is realized by the hardware, likewise in another embodiment, the steps or methods may be realized by one or a combination of the following techniques known in the art: a discrete logic circuit having a logic gate circuit for realizing a logic function of a data signal, an application-specific integrated circuit having an appropriate combination logic gate circuit, a programmable gate array (PGA), a field programmable gate array (FPGA), etc.

Those skilled in the art shall understand that all or parts of the steps in the above exemplifying method of the present disclosure may be achieved by commanding the related hardware with programs. The programs may be stored in a computer readable storage medium, and the programs comprise one or a combination of the steps in the method embodiments of the present disclosure when run on a computer.

In addition, each function cell of the embodiments of the present disclosure may be integrated in a processing module, or these cells may be separate physical existence, or two or more cells are integrated in a processing module. The integrated module may be realized in a form of hardware or in a form of software function modules. When the integrated module is realized in a form of software function module and is sold or used as a standalone product, the integrated module may be stored in a computer readable storage medium.

The storage medium mentioned above may be read-only memories, magnetic disks, CD, etc.

Although explanatory embodiments have been shown and described, it would be appreciated by those skilled in the art that the above embodiments cannot be construed to limit the present disclosure, and changes, alternatives, and modifications can be made in the embodiments in the scope of the present disclosure.

What is claimed is:

1. A Field-Programmable Gate Array (FPGA)-based resequencing analysis method, comprising:
   receiving genome resequencing data;
   taking the genome resequencing data as an input of an FPGA, determining an alignment result in a process of resequencing based on an output of the FPGA, and at the same time, sorting and deduplicating the alignment result;
   subjecting a sorted and deduplicated alignment result to correction in accordance with a base quality value; and
   detecting a variation result based on a corrected alignment result.

2. The FPGA-based resequencing analysis method of claim 1, wherein subsequent to receiving genome resequencing data, the method further comprises:
   subjecting the genome resequencing data to hash-calculation based on a sequence of a preset length,
   taking the genome resequencing data as an input of an FPGA further comprising
   taking hash-calculated genome resequencing data as the input of the FPGA.

3. The FPGA-based resequencing analysis method of claim 1,
   wherein the genome resequencing data comprises basic genome resequencing data and parameter information describing the basic genome resequencing data,
   wherein subsequent to receiving genome resequencing data, the method further comprises:
   determining a first task for outputting the alignment result and a second task for sorting and deduplicating the alignment result based on the basic genome resequencing data and the parameter information describing the basic genome resequencing data; and
   allocating a first thread corresponding to the first task from the FPGA and a second thread corresponding to the second task from a CPU.

4. The FPGA-based resequencing analysis method of claim 3, wherein taking the genome resequencing data as an input of an FPGA, determining an alignment result in a process of resequencing based on an output of the FPGA, and at the same time, sorting and deduplicating the alignment result further comprises:
   starting and executing the first thread corresponding to the first task and the second thread corresponding to the second task in parallel, such that the genome resequencing data is called via respective threads; and
   determining the alignment result in the process of resequencing via an output result of the first thread corresponding to the first task, and at the same time, sorting and deduplicating the alignment result via an output result of the second thread corresponding to the second task.

5. The FPGA-based resequencing analysis method of claim 4, wherein determining the alignment result in the process of resequencing via an output result of the first thread corresponding to the first task further comprises:
   executing the first thread corresponding to the first task to determine a targeted alignment position;
   triggering alignment on duplicate base pairs in the basic genome resequencing data in accordance with the targeted alignment position; and
   taking an alignment result of the duplicate base pairs as the alignment result in the process of resequencing.

6. The FPGA-based resequencing analysis method of claim 4, wherein subsequent to determining a targeted alignment position, the method further comprises:

caching the targeted alignment position by using a ping-pong buffering technology.

7. A computer device, comprising:
a memory;
a processor; and
a computer program stored in the memory and executable by the processor,
wherein the computer program, when executed by the processor, achieves a Field-Programmable Gate Array (FPGA)-based resequencing analysis method,
wherein the method comprises:
receiving genome resequencing data;
taking the genome resequencing data as an input of an FPGA, determining an alignment result in a process of resequencing based on an output of the FPGA, and at the same time, sorting and deduplicating the alignment result;
subjecting a sorted and deduplicated alignment result to correction in accordance with a base quality value; and
detecting a variation result based on a corrected alignment result.

8. A non-transitory computer-readable storage medium having stored therein computer-readable instructions that causes the computer to perform a Field-Programmable Gate Array (FPGA)-based resequencing analysis method,
wherein the method comprises:
receiving genome resequencing data;
taking the genome resequencing data as an input of an FPGA, determining an alignment result in a process of resequencing based on an output of the FPGA, and at the same time, sorting and deduplicating the alignment result;
subjecting a sorted and deduplicated alignment result to correction in accordance with a base quality value; and
detecting a variation result based on a corrected alignment result.

* * * * *